United States Patent
Warburton et al.

(10) Patent No.: US 6,742,382 B2
(45) Date of Patent: Jun. 1, 2004

(54) COMBUSTIBLE GAS DETECTOR AND METHOD FOR ITS OPERATION

(75) Inventors: P. Richard Warburton, Moon Township, PA (US); Chuan-Bao Wang, Oakdale, PA (US)

(73) Assignee: Industrial Scientific Corporation, Oakdale, PA (US)

(*) Notice: Subject to any disclaimer, the term of this patent is extended or adjusted under 35 U.S.C. 154(b) by 0 days.

(21) Appl. No.: 10/327,490

(22) Filed: Dec. 24, 2002

(65) Prior Publication Data

US 2003/0159497 A1 Aug. 28, 2003

Related U.S. Application Data

(60) Provisional application No. 60/360,017, filed on Feb. 28, 2002.

(51) Int. Cl.[7] .................. G01N 7/00; G01N 33/00; G01N 33/497
(52) U.S. Cl. .................. 73/23.31; 436/143
(58) Field of Search .................. 73/23.2, 23.31, 73/31.05, 31.07; 422/98; 436/143, 156, 159

(56) References Cited

U.S. PATENT DOCUMENTS

| | | | | |
|---|---|---|---|---|
| 4,305,724 A | * | 12/1981 | Micko | 436/156 |
| 4,475,378 A | * | 10/1984 | Boutonnat et al. | 73/23.31 |
| 4,562,723 A | * | 1/1986 | Hubner | 73/31.07 |
| 4,569,223 A | * | 2/1986 | Hubner | 73/23.2 |
| 4,804,632 A | * | 2/1989 | Schuck et al. | 436/143 |
| 5,012,432 A | * | 4/1991 | Stetter et al. | 702/136 |
| 5,055,270 A | * | 10/1991 | Consadori et al. | 422/98 |
| 5,234,837 A | * | 8/1993 | Accorsi et al. | 436/159 |
| 5,709,792 A | * | 1/1998 | Zdanevitch et al. | 205/775 |
| 5,918,260 A | * | 6/1999 | Newman et al. | 73/31.05 |

* cited by examiner

Primary Examiner—Hezron Williams
Assistant Examiner—C D Garber
(74) Attorney, Agent, or Firm—Dennison, Schultz, Dougherty & MacDonald

(57) ABSTRACT

A catalytic bead sensor or a semiconductor sensor is operated in a manner in which the power requirement is greatly reduced. The reduction in power is accomplished by operating the sensor at a temperature less than the desired operating temperature in the absence of a combustible gas and increasing to the desired operating temperature when the sensor is exposed to a combustible gas.

24 Claims, 7 Drawing Sheets

COMBUSTIBLE GAS DETECTOR AND METHOD FOR ITS OPERATION

This application claims the benefit of Provisional Application No. 60/360,017 filed Feb. 28, 2002.

BACKGROUND OF THE INVENTION

1. Field of the Invention

The invention relates to a method of reducing power for a catalytic bead or semiconductor sensor in a gas detector by operating the sensor at a temperature lower than the desired operating temperature in the absence of a combustible gas and increasing the temperature to the desired operating temperature for accurate measurement when the sensor detects a combustible gas.

2. Description of Related Art

Gas detectors including catalytic bead (pellistor) sensors or semiconductor (MOS) sensors are widely used to detect the presence of combustible gases or vapors for safety and environmental purposes and to provide a warning of potentially explosive conditions to protect life and properties.

A catalytic bead sensor typically contains two ceramic beads coated onto platinum wire coils, a sensing bead and a compensating bead. The sensing bead is impregnated with a noble metal catalyst, which promotes combustion of the combustible gases or vapors, while the compensating bead does not contain a catalyst, but compensates for environmental effects such as humidity and ambient temperature. The sensor is typically connected to two arms of a Wheatstone bridge. When a voltage is applied across the bridge, resistive heating of the platinum wire coils and hence the beads takes place. In the presence of a combustible gas or vapor, catalytic combustion takes place on the sensing bead and generates combustion heat, causing an increase in the bead temperature and thus the sensing bead wire resistance. The Wheatstone bridge measures changes in the resistance of the sensing bead wire resistance and thus provides an output signal. Detailed descriptions on this type of gas sensor can be found, for example, in U.S. Pat. Nos. 3,200,011, 3,092,799, 4,313,907 and 4,416,911, and in Mosley, P. T. and Tofield, B. C., "Solid State Gas Sensors", Adams Hilger Press, Bristol, England (1987).

A catalytic bead sensor is typically operated at a desired temperature of about 500° C. with a power consumption of 230–350 mW for portable gas detectors. The desired operating temperature of about 500° C. is chosen so that all combustible gases, including methane, that require the highest bead temperature can be detected, and so that the sensor is operated under diffusion-limited conditions to provide the best accuracy and stability. The runtime of a portable gas detector operated by a battery pack is typically 10–20 hours and is largely determined by battery capacity and power usage. It would be desirable to design a portable gas detector with a small battery size and a small detector size, and therefore it would be extremely desirable to operate a catalytic bead sensor at significantly reduced power.

Several approaches have been described in the prior art to reduce the operating power of the catalytic bead sensor:

1) The first approach is to design a catalytic bead sensor that consumes low power. For example, it has been reported that a catalytic sensor fabricated by silicon micro-machining techniques has power consumption as low as 60 mW. The micro-machined catalytic sensor, however, typically possesses a very low resistance to catalyst poisons and thus a short lifetime. Furthermore, commercial micro-machined catalytic sensors are rarely available at this time. Examples of such a sensor are described in Krebs, P., and Grisel, A., Sensors and Actuators B, 13–14, 155–158 (1993); U.S. Pat. Nos. 5,813,764, 5,820,922 and 5,599,584; European Patent Application EP 0,697,593A1; and PCT application WO 00/14307.

2) The second approach is to use a catalytic bead sensor that is comprised of only a sensing bead, which is expected to reduce power to half of that for a two-bead catalytic sensor at the expense of performance. A gas detector with a single bead sensor typically has a large response to ambient temperature and humidity. For example, the Model GX-2001 of RKI Instruments, Inc. (Japan) uses such a single bead catalytic sensor.

3) The third approach is to apply pulsed power to a catalytic bead sensor. Since it typically takes 2 seconds to reach the desired operating temperature, pulse operation typically allows updating the signal output once every few seconds instead of a continuously updating signal output. For example, the Model GX-2001 of RKI Instruments, Inc. (Japan) also uses pulsed power to reduce power consumption. Examples of using pulsed power for a catalytic bead sensor are described in Japanese Provisional Utility Model Publication No. 14595, Japanese Provisional Patent Publication No. 03-233699 and U.S. Pat. Nos. 4,020,480, 6,348,872.

4) The fourth approach is to use a catalytic bead sensor in conjunction with an oxygen sensor as described in U.S. Pat. No. 6,442,994. When the oxygen sensor indicates an expected oxygen concentration in ambient atmosphere, the catalytic bead sensor is turned off, and when the oxygen sensor indicates a reduced oxygen concentration, which means some of the oxygen may have been displaced by a combustible gas, the catalytic bead sensor is turned on. However, this method depends on oxygen concentration in ambient environment and thus is only an indirect detection of the presence of a combustible gas. Furthermore, some combustible gases with very small Lower Explosive Limits (LEL) can lead to only small changes in the output signal of the oxygen sensor, which are within the variation range of the oxygen sensor in ambient atmosphere. Thus, relying on variations in the oxygen sensor output is potentially dangerous.

5) The fifth approach is to use a battery management scheme that allows efficient use of battery power. Examples of the battery power managing methods are described in U.S. Pat. No. 6,252,375 and Electronic Engineering Times, 72 (2002-01-07). The Scout MultiGas Monitor of Scott Technologies, Inc. applies this approach to extend the run time up to 50 hours.

Semiconductor sensors, which are based on metal oxide semiconductors such as tin oxide, for detecting combustible gases are well known in the prior art. They rely on adsorption of a combustible gas onto a heated oxide surface with a desired temperature in the range of typically 100–500° C. The adsorption produces an electric conduction change in the metal oxide itself, which are related to the concentration of a combustible gas in surrounding atmosphere. A semiconductor sensor is typically composed of an electric heater, two electrodes, and a metal oxide bead surrounding the heater and electrodes. Power consumption is also an important concern when this type of sensor is used in a portable gas detector.

Therefore, it is desirable to have a method of significantly reducing power for a catalytic bead sensor or a semiconductor sensor, which can be used with commercially available combustible gas sensors and allow for continuous measurement of the atmosphere to be monitored.

SUMMARY OF THE INVENTION

It is therefore an object of the invention is to provide a method to significantly reduce power consumption of a catalytic bead sensor or a semiconductor sensor.

Another object of the invention is to provide a power reduction method that allows for direct measurement of a combustible gas.

A further object of the invention is to provide a power reduction method that can be used with commercially available combustible gas sensors.

A still further object of the invention is to provide a method to operate a catalytic bead or semiconductor sensor at reduced power while retaining sensor performance in accuracy, repeatability, response time, and poisoning resistance.

A still further object of the invention is to provide a method to operate a catalytic bead sensor or a semiconductor sensor at reduced power while increasing sensor lifetime by reducing catalyst-sintering rate.

According to the invention, power reduction is accomplished by operating a sensor which utilizes a heated surface, at a temperature which is lower than a defined, desired operating temperature for a period of time during which combustible gas, as defined by an electrical parameter output of the sensor, is below a threshold level. When the combustible gas level detected by the sensor is at least the threshold level, the operating temperature of the sensor is increased to the desired operating temperature. The lower temperature is a temperature at which the sensor operates, i.e. a temperature at which the gas is oxidized on the sensor surface, but a temperature at which accuracy and/or stability of the sensor is not adequate for normal operation.

Adjustment of the operating temperature of the sensor is accomplished by varying the parameters of the electrical supply to the sensor. Thus, voltage, current, or power is supplied, which is lower than the voltage, current, or power necessary to raise the sensor to the desired operating temperature.

The sensor of the invention may include both a sensing element and a compensating element, or may include only a sensing element.

According to an aspect of the invention, power reduction is accomplished by operating a sensor with pulses of electricity, where the duration of the pulse is adjusted, optionally in combination with the pulse voltage, current or power, to achieve an operating temperature which is lower than the desired operating temperature to save energy in the absence of a combustible gas or to achieve the desired operating temperature in the presence of a combustible gas.

According to another aspect of the invention, a sensor is calibrated at the desired operating temperature, and preferably also calibrated at the lower operating temperature, with a known concentration of a combustible gas.

According to a further aspect of the invention, the sensor is periodically switched from the lower operating temperature to the desired operating temperature to clean the sensor surface by removing adsorbed compounds.

DESCRIPTION OF THE PREFERRED EMBODIMENTS

Figure 1:
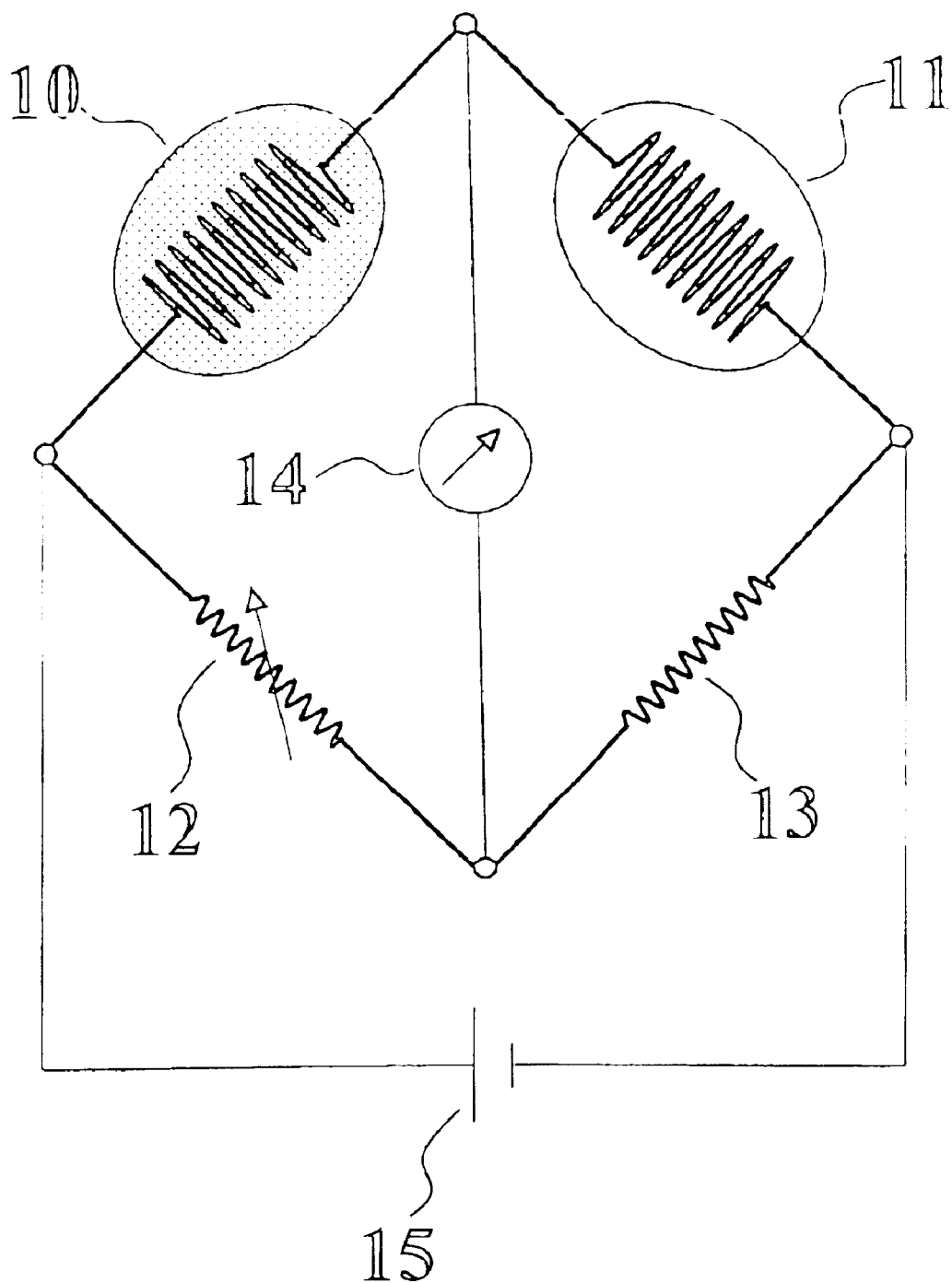
FIG. 1 is a schematic diagram of a prior art Wheatstone bridge circuit.

FIG. 1 illustrates the working principle of a prior art catalytic bead sensor, where a sensing element 10 is connected into one arm of a Wheatstone bridge circuit, the other three arms being constituted by a compensating bead 11, a variable resistor 12, and a fixed resistor 13 having a value such that the bridge can be balanced by adjustment of resistor 12. Across the two diagonals of the bridge are respectively connected a voltmeter 14 and a voltage source 15. The output voltage of the source 15 is chosen so as to heat the sensing element 10 and the compensating bead 11 to a desired operating temperature (~500° C.) at which all combustible gases, including methane, will burn. The variable resistor 12 is adjusted so that the voltmeter 14 indicates a zero reading when the sensing element 10 and the compensating bead 11 are exposed to a clean atmosphere without any combustible gases. The voltmeter 14 is calibrated by exposing the sensing element 10 and the compensating bead 11 to a known combustible gas concentration and then to the atmosphere to be monitored. Any combustible gas present in the atmosphere will catalytically burn on the surface of the sensing element 10 but not on the surface of the compensating bead 11, causing the temperature of the sensing element 10 to rise with a consequent change in its resistance. This increase in resistance causes a change in the potential across the voltmeter 14, which then provides a measure of combustible gas concentration.

Figure 2:
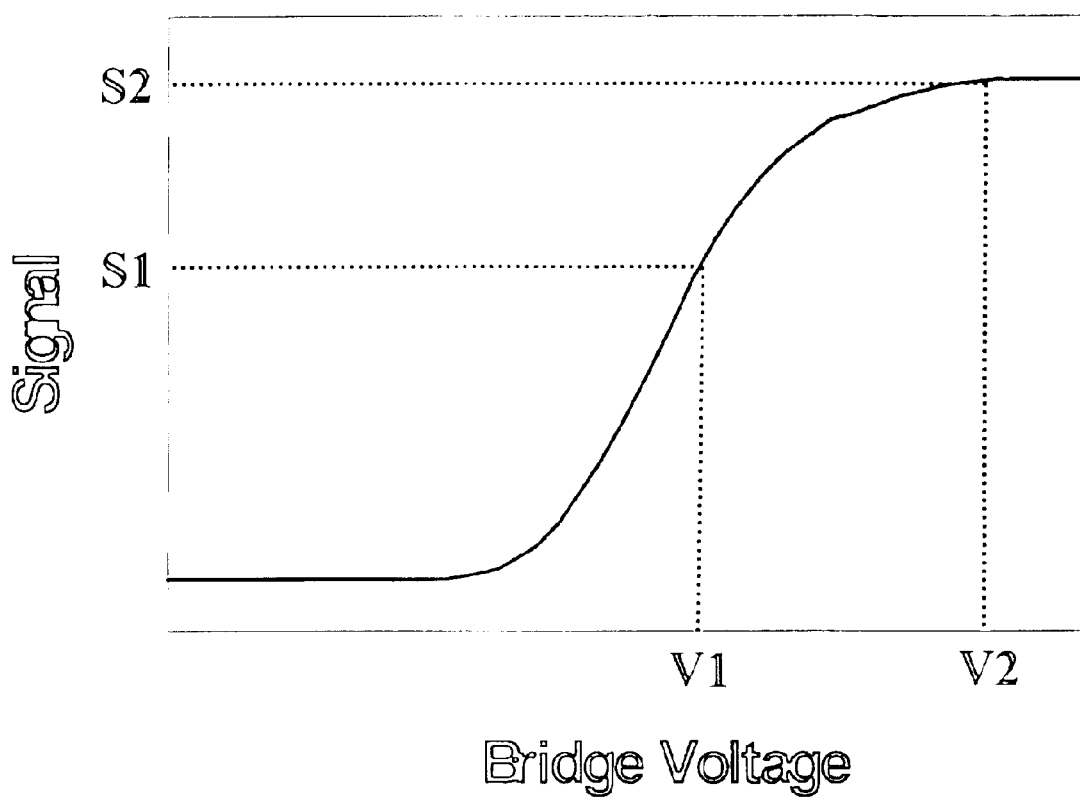
FIG. 2 is a sensitivity vs. bridge voltage curve for a catalytic bead sensor in the presence of a combustible gas.

In a desired operating mode (FIG. 2), the sensor is operated at a voltage V2, at which the sensing bead reaches a desired operating temperature (~500° C.) and all of any combustible gas that reaches the catalytic bead is essentially burned. Since the output is diffusion-limited, it reaches the maximum sensitivity (S2) and has the greatest tolerance to the dynamic nature of catalyst and the variations in applied voltage. These factors combine to give the best response and the best accuracy to a measured gas when the sensor is operated under diffusion-limited conditions. However, at the desired operating voltage (V2), the power requirement of the sensor is relatively large.

If the sensor is operated at a lower voltage V1 that will result in a lower operating temperature, the sensitivity is reduced, and the response characteristics are generally worse than those at V2. The lower operating temperature is in the range of 200–450° C., and more preferably in the range of 300–400° C. so that the sensor can still detect the presence of methane.

The invention disclosed herein is advantageous in that it enables operating the sensor in the diffusion-limited range (V2), but the power consumption of the sensor is significantly lowered.

In one embodiment of the invention, a catalytic bead sensor in a Wheatstone bridge circuit is operated at reduced voltage V1 and thus reduced power compared to the desired operating voltage V2. In our testing, we have successfully run the sensor at about half of the desired power. However, the power reduction will depend on many factors, including the design of the sensor, the long-term stability of the sensor, the susceptibility to catalyst poisons and inhibitors, and the sensitivity of instrument. At V1, the signal output or sensitivity S1 of the sensor towards methane is still large enough to provide a measurable signal. In this invention, when the sensor detects the presence of a combustible gas, the operating voltage is automatically increased to the desired operating voltage V2 to accurately measure the concentration of the combustible gas. If the gas is removed, the power returns to the lower voltage V1. Thus, the higher voltage V2 and hence higher power mode of operation of the sensor is only used in the presence of a combustible gas.

Most combustible gas sensors are used for safety monitoring, and thus are predominantly exposed to ambient air that is essentially free of combustible gases with only occasional exposure to atmospheres containing combustible gases. Thus, the power savings achieved by operating the sensor at V1 compared to V2 can be substantial.

Figure 3:
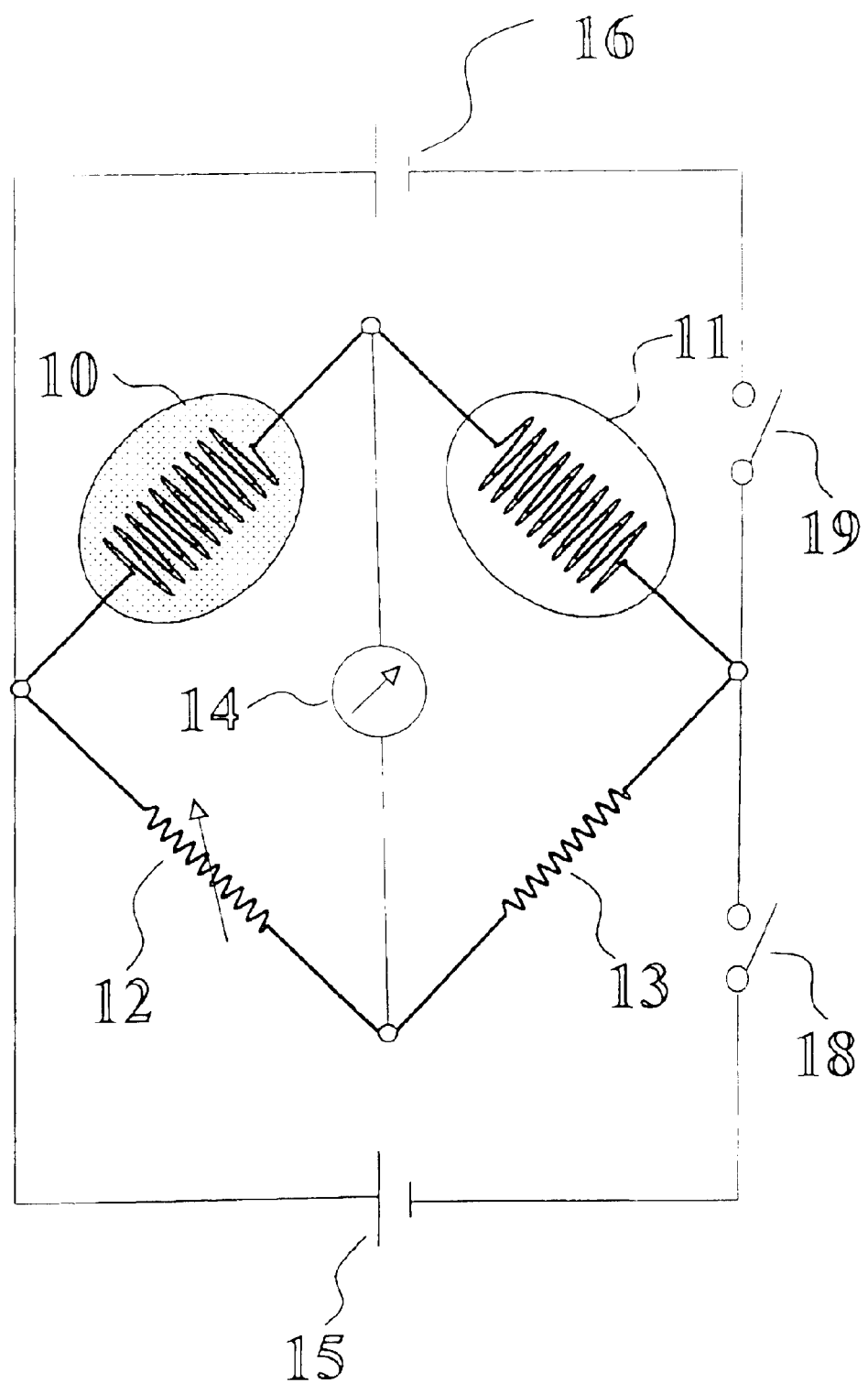
FIG. 3 is a schematic diagram of an embodiment of the invention, in which a catalytic bead sensor is used in a modified Wheatstone bridge circuit.
Figure 4:
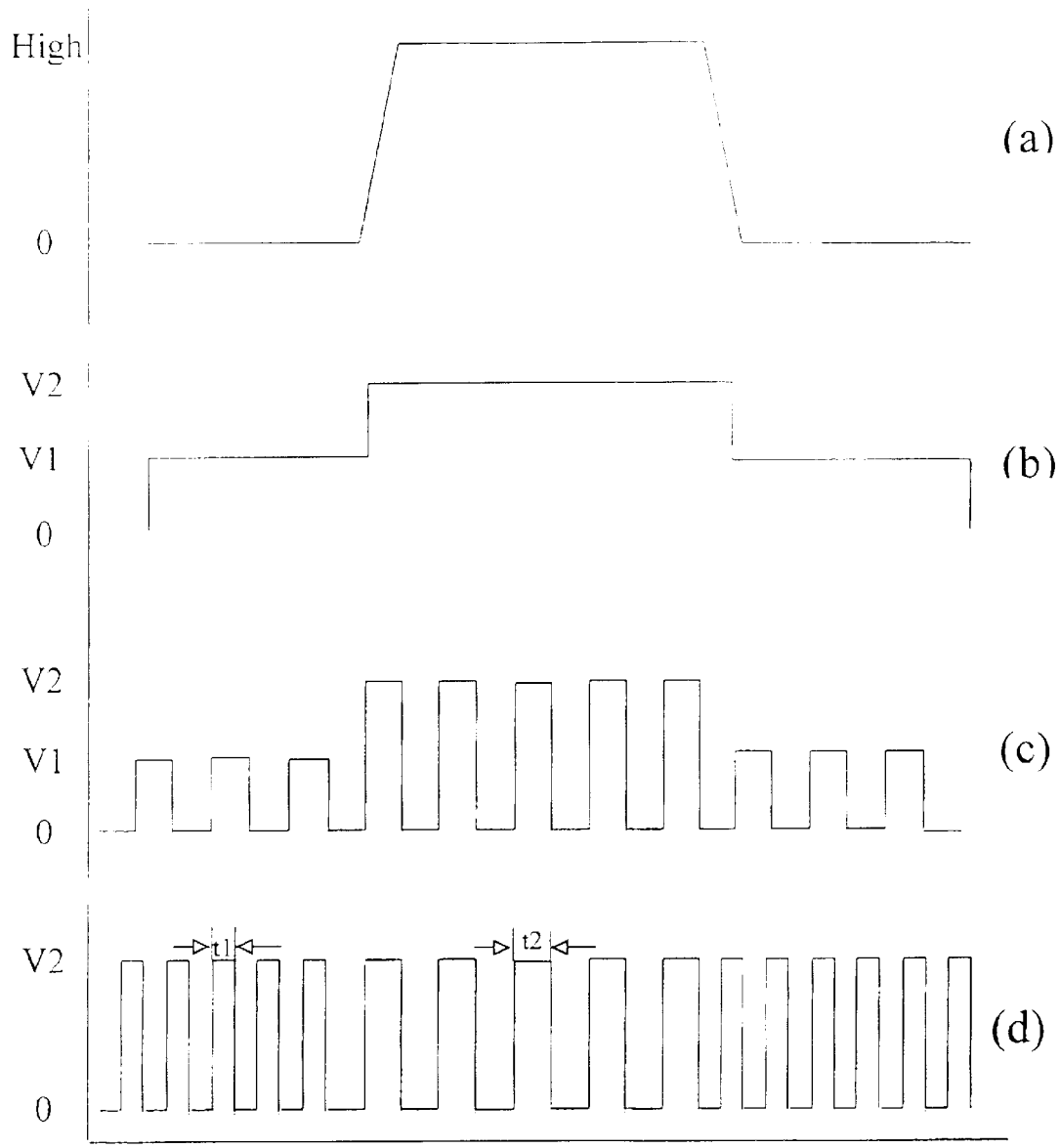
FIG. 4 is a graph showing a gas concentration profile and three electric power profiles to illustrate embodiments of this invention.

FIG. 3 further illustrates this embodiment, wherein the voltage source 16 corresponds to V1 and the voltage source 15 to V2. The operation of the device is shown in FIG. 4, where the gas concentration profile is represented by curve a, and the corresponding voltage profile of this embodiment is represented by curve b. In routine operation and in the absence of a combustible gas, switch 19 is closed to apply voltage V1 and switch 18 is open. The operating voltage will be switched from V1 to V2 when the sensor detects the presence of a combustible gas. In practice, switches 18 and 19 are operated by an electric control element (not shown), which can be a microprocessor, computer, logic circuit, or other conventional control means. The output from the bridge is measured at voltmeter 14 and monitored by the measurement element (not shown). If the output exceeds a predetermined threshold, then the control element will cause switch 19 to close and switch 18 to open at the same time. Closing switch 15 connects the bridge to voltage source 15 at which the sensor operates under essentially diffusion control mode and the sensor output has optimum accuracy. The sensor continues to operate from voltage source 15 until the output signal from voltmeter 14 declines below a predetermined set point, at which point the control element causes switch 18 to open and switch 19 to close at the same time.

The predetermined set point for switching between switches 18 and 19 is chosen based on the signal-to-noise ratio of the output signal, the effects of ambient conditions such as temperature and humidity on the output signal, and the alarm settings of the instrument. For example, a typical commercial catalytic bead sensor possesses a response in the range of ±3% LEL when there is a change in temperature and/or humidity in ambient atmosphere. The instrument alarm is typically set at a level of 10% LEL. The set point for switching power applied to the sensor is preferably 3–5% LEL, which is higher than sensor's response to changes in ambient conditions, and lower than the alarm setting when sensor output signal rises.

Furthermore, in practice, it is advantageous to set the set point at which the bridge voltage changes from V1 to V2 to be about 50 mV higher than the set point at which the bridge voltage changes from V2 to V1 to reduce the possibility of oscillation.

The circuit shown in FIG. 3 is drawn in simplified form to show the key features of this invention. It is recognized that many alternative circuits that perform similar functions and provide electric heating in the form of voltage, current, or power can be readily devised by those experienced in the art of electronic design. They include: (1) other forms of Wheatstone bridge circuits; (2) constant power circuits; (3) constant current circuits; (4) varied power circuits; (5) pulse power circuits; and (6) an Anderson loop, described in Anderson, K. F., ISA-Tech 97, Anaheim, Calif., October 1997.

According to the invention, a sensor is at least calibrated at the desired operating voltage, current, or power with a known concentration of a combustible gas. It is preferable to calibrate the sensor both at a voltage, current, or power lower than the desired operating voltage, current, or power and at the desired operating voltage, current, or power with a known concentration of a combustible gas.

According to the invention, periodic switching from V1 to V2 can be applied in the absence of a combustible gas in order to clean the catalyst surface, on which some compounds from an atmosphere may be adsorbed. The desired operating temperature at V2 will facilitate full combustion of the adsorbed compounds on the catalyst surface. For example, cleaning can be done on daily basis when a gas detector is turned on.

The lifetime of a catalytic bead sensor operated according to the invention is extended. One of the common failure modes of catalytic bead sensors is deactivation of the catalyst due to sintering. It is well known that the catalyst in the sensing bead sinters at a lower rate when the operating temperature is lower, and thus lower operating temperature extends the sensor lifetime.

Therefore, in this embodiment a gas detector installed with a catalytic bead sensor detects a combustible gas by a procedure including the steps of:

operating a sensor at a voltage V1 that is lower than the desired operating voltage in the absence of a combustible gas;

switching to a voltage V2 that is the desired operating voltage for accurate measurement when the gas detector detects the presence of a combustible gas; and switching back from V2 to V1 when the combustible gas is removed.

This invention can be combined with other known methods of reducing the power consumption of a catalytic bead or semiconductor sensors. In most cases the power saved by use of both methods is additive. To illustrate this synergy of methods, several embodiments of the invention are described.

In the second embodiment of the invention, pulses of electricity V1 and V2 are used to power a catalytic bead sensor, as shown in curve c of FIG. 4. The ON time is chosen so that the sensor can reach the desired operating temperature when the pulse V2 is applied. We have found experimentally that a time of approximately 2 seconds works well, but the ON time of the pulsed power depends upon the properties of a specific sensor. The OFF time is a few seconds depending on how much power to be saved and the maximum time allowed between measurements. In this embodiment, a gas detector detects a combustible gas by a procedure including the steps of:

operating a sensor at a pulsed voltage V1, the magnitude of which is lower than that of the desired pulsed operating voltage, in the absence of a combustible gas;

switching to a pulsed voltage V2 that is the desired pulsed operating voltage for accurate measurement when the gas detector detects the presence of a combustible gas; and switching back from pulsed voltage V2 to pulsed voltage V1 when the combustible gas is removed.

In the third embodiment of the invention shown in curved of FIG. 4, pulses V2 with a duration of time t1 and pulses V2 with a duration of t2 are used to power a catalytic bead sensor. The duration t2 is ~2 seconds so that the sensor can reach the desired operating temperature when the pulses V2 are applied. The duration t1 is shorter than t2 and is not long enough to heat the sensor to the desired operating temperature. According to this embodiment, a gas detector detects a combustible gas by a procedure including the steps of:

operating a sensor at a pulsed V2 with a duration of t1 in the absence of a combustible gas;

switching to a pulsed voltage V2 with a duration of t2 for accurate measurement when the gas detector detects the presence of a combustible gas; and switching back from t2 to t1 when the combustible gas is removed.

In the fourth embodiment of the invention, a catalytic bead sensor in a Wheatstone bridge is operated in such a way that only the sensing bead is powered at half of V1, that is, lower than the desired operating voltage, and the compensating bead is not on power in the absence of a combustible gas. In our laboratory testing, this configuration has typically yielded power savings of about 75%. When the sensing bead detects a combustible gas, the voltage is switched to V2 to power both the sensing bead and the compensating bead for accurate measurement.

Figure 5:
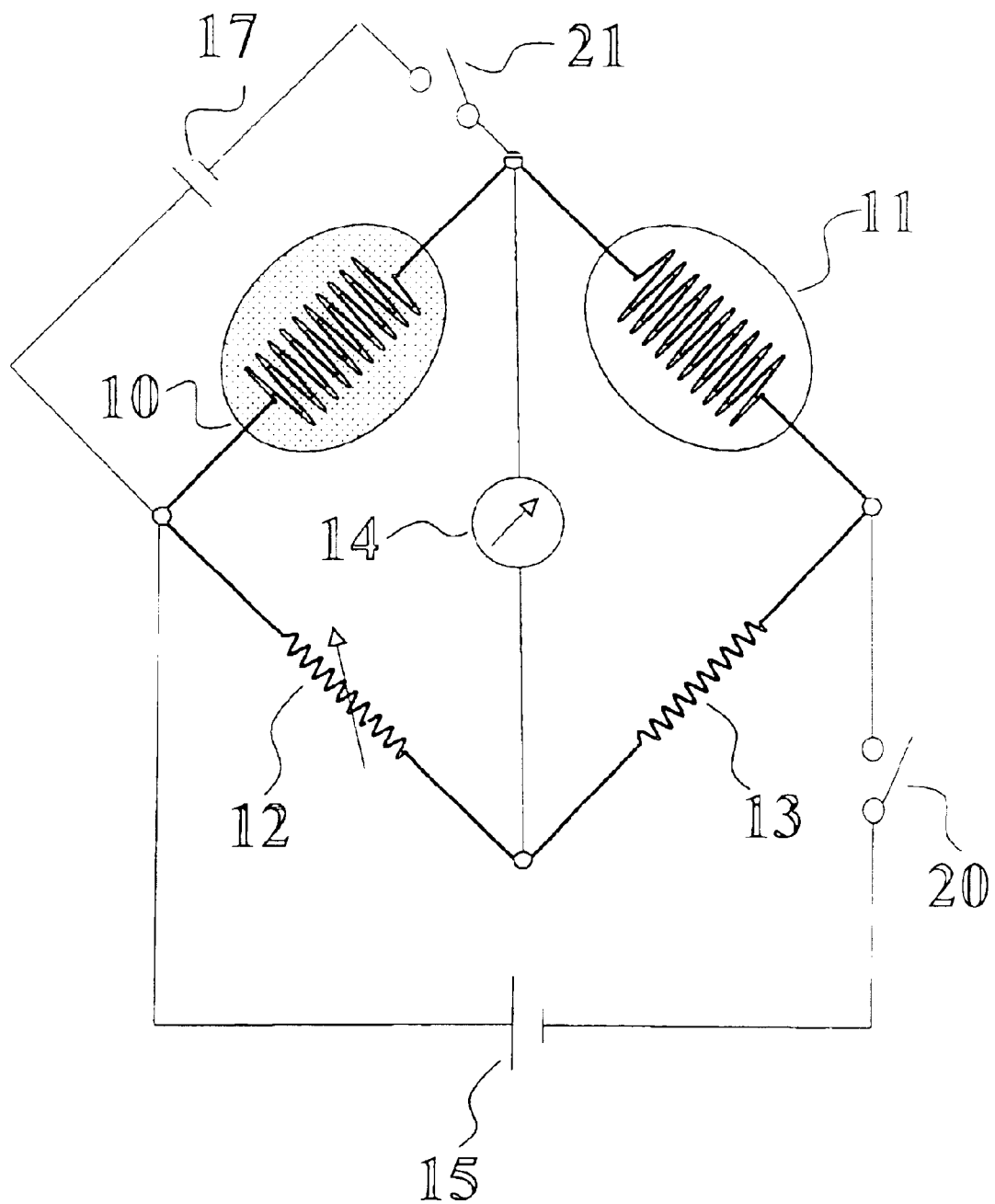
FIG. 5 is a schematic diagram of another embodiment of the invention, in which a catalytic bead sensor is used in a modified Wheatstone bridge circuit.

FIG. 5 illustrates the working principle of this embodiment. When there is no combustible gas present in an atmosphere, the sensor is operated with switch 21 closed and switch 20 open. In this configuration, only the sensing bead 10 is powered at half of V2, and the compensating bead 11 is unpowered. The presence of a combustible gas causes change in resistance of the sensing bead, which is measured by a measurement circuit (not shown). When the resistance change exceeds a predetermined set point, switch 21 is opened and switch 20 is closed essentially at the same time. With switch 20 closed, both the sensing bead 10 and the compensating bead 11 are operated at V2. Voltage source 15 provides a bridge voltage V2 at which the sensor is operated at the desired operating temperature and detects gas under diffusion-limited conditions and thus provides the maximum accuracy.

The sensor continues to operate from voltage source 15 until the output signal from the resistance measurement circuit declines below a predetermined set point, at which point the control element causes switch 20 to open and switch 21 to close essentially at the same time. Typically, the set point at which the voltage changes from voltage source 15 to voltage source 17 will be less than or equal to the set point at which the voltage changes from voltage source 17 to voltage source 15. In practice, it is advantageous to set the set point at which the voltage changes from voltage source 15 to voltage source 17 to be about 50 mV less than the set point at which the voltage changes from voltage source 17 to voltage source 15.

According to this embodiment, the voltage sources 15 and 17 in FIG. 5 can be pulsed voltage sources. The duration of the pulses is about 2 seconds, which is long enough for the sensing bead to reach the desired operating temperature (~500° C.) when pulses V2 are applied. The routine operating temperature at pulses V1 is lower than the desired operating temperature.

Figure 6:
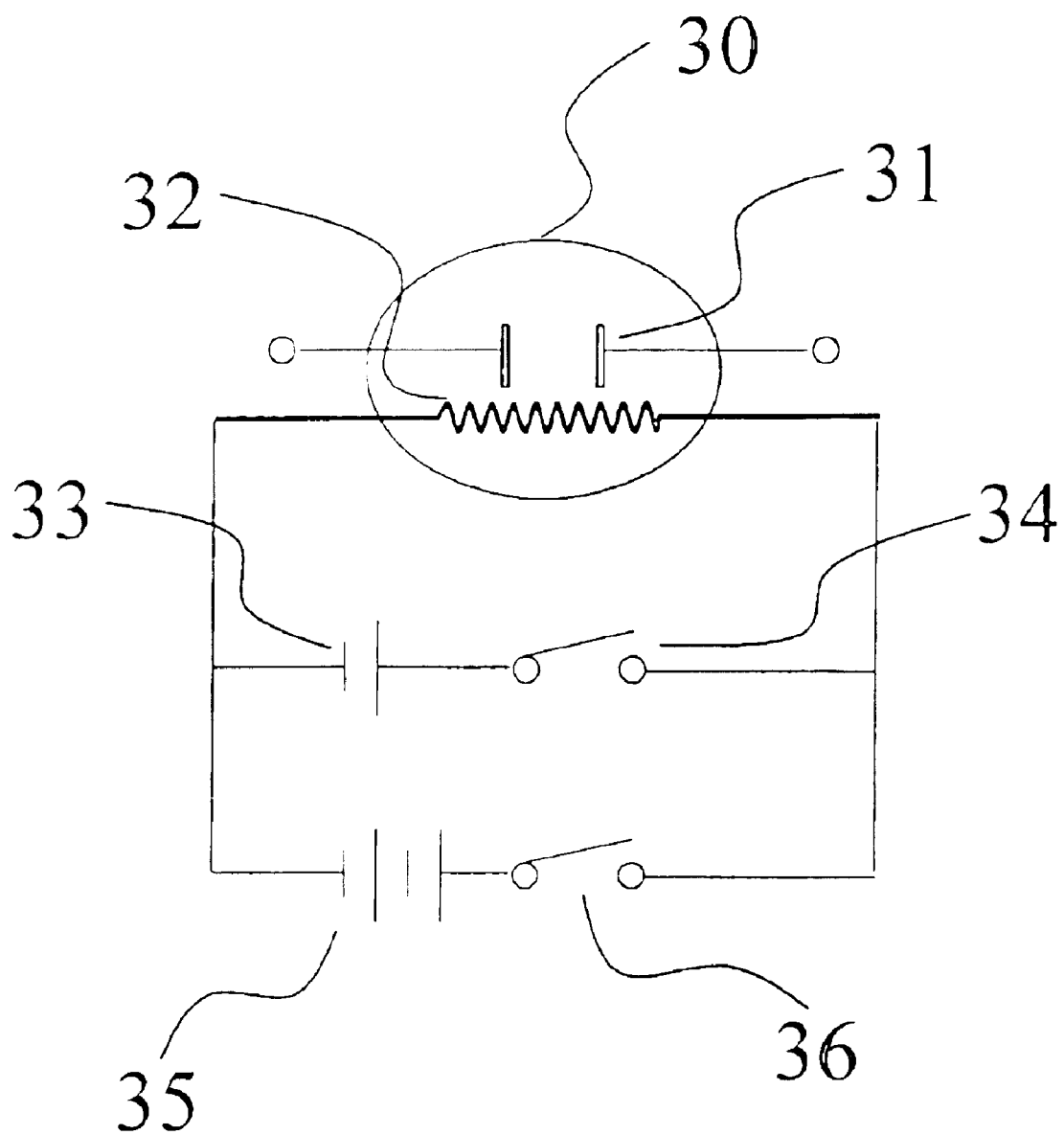
FIG. 6 is a schematic diagram of another embodiment of the invention, in which a semiconductor sensor is used in a simplified circuit.

In the fifth embodiment of this invention, a metal oxide semiconductor sensor is used instead of a catalytic bead sensor for a gas detector. FIG. 6 illustrates the working principle of this embodiment, where a sensing element 30 is heated by an electric heater 32 and a pair of electrodes 31 is used to measure changes in electric resistance of the metal oxide in the sensing element. According to this embodiment, a gas detector installed with a semiconductor sensor detects a combustible gas by a procedure including the steps of:

operating a sensor at V1 that is lower than the desired operating voltage by closing switch 34 and opening switch 36 in the absence of a combustible gas;

switching to V2 that is the desired operating voltage by closing switch 36 and opening switch 34 for accurate measurement when the gas detector detects the presence of a combustible gas; and switching back from V2 to V1 by closing switch 34 and opening switch 36 when the combustible gas is removed.

In this embodiment of the invention, pulses V1 and V2 can also be used to operate a semiconductor sensor in a gas detector. A pulsed power source with different durations of t1 and t2 can also be used to operate a semiconductor sensor.

Figure 7:
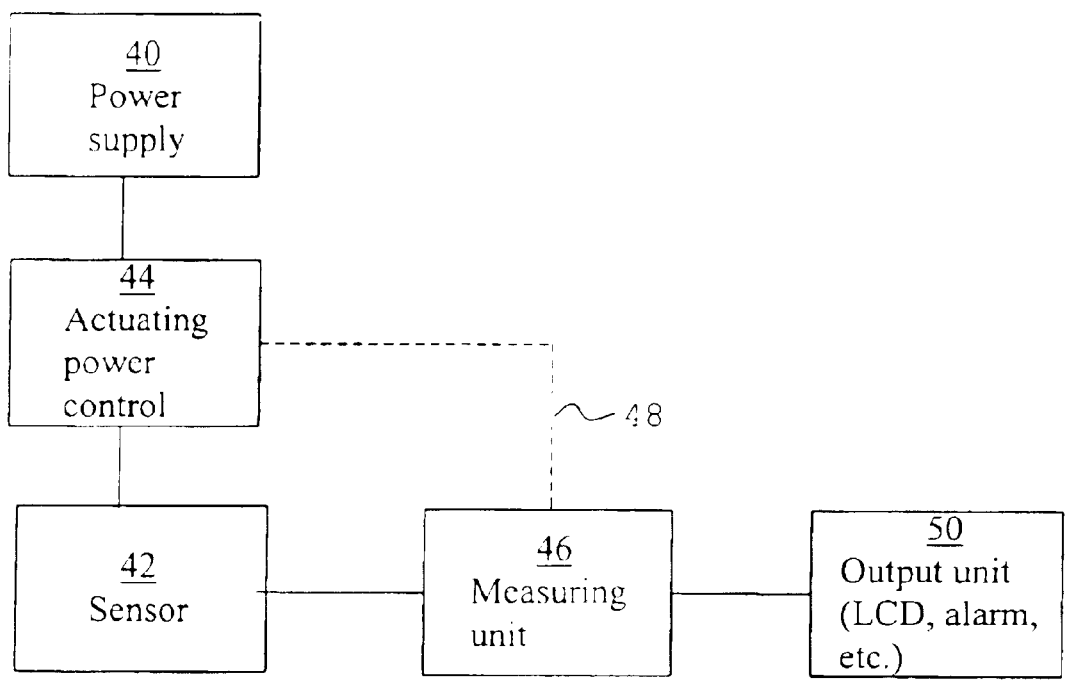
FIG. 7 is a schematic diagram showing connection of the units needed to perform the method of the invention.

The connection of the units necessary to operate the invention is shown in FIG. 7, in which there is a power supply 40 connected to sensor 42 by way of an actuating power control 44. The sensor output is sent to a measuring unit 46 that is connected by a feedback link 48 to the actuating power control. An output unit 50, as is well known in the art, provides an audible and/or visible indication of the presence of a combustible gas.

EXAMPLE

Operating a Commercial Catalytic Bead Sensor with Voltages V1 and V2

A commercial catalytic bead sensor was tested experimentally at V1=1.6 V and V2=2.15 V to address many issues of this invention and the results are summarized below:

Signal output was determined in response to different combustible gases and levels of humidity. The signal output to methane, pentane, and acetylene at 1.6 V is 56.6%, 92.0%, and 99.1% of that at 2.15 V, respectively (see TABLE 1). Therefore, there is no problem detecting the presence of these three gases when the sensor is operated at 1.6 V. Actually, as long as the sensor is able to detect methane, it can detect all other combustible gases since methane is the most inert and thus the most difficult to be detected. The response to 90% relative humidity is smaller at 1.6 V than 2.15 V, indicating that the sensor can be operated at low temperature with less disturbance by humidity.

TABLE 1

| Test gas | Signal at 2.15 V | Signal at 1.60 V | Signal ratio of 1.6 to 2.15 V |
|---|---|---|---|
| 2.5% methane (mV/% LEL) | 0.53 | 0.32 | 56.6% |
| 0.35% pentane (mV/% LEL) | 0.24 | 0.22 | 92.0% |
| 0.63% acetylene (mV/% LEL) | 0.40 | 0.40 | 99.1% |
| 90% RH (mV) | 0.10 | 0.29 | 34.5% |

A catalytic bead sensor is susceptible to poisoning by catalyst poisons such as silicon and sulfur. The poisoning rate at 1.6 V and 2.15 V was compared by exposing the sensor to a flow of 9.5 ppm hexamethyldisiloxane (HMDS) or 1000 ppm hydrogen sulfide ($H_2S$). After 2.5 hours, the signal reductions at 1.6 V and 2.15 V were summarized in TABLE 2. The results show that the sensor was poisoned by HMDS at a similar rate when it was operated at 1.6V and at 2.15V. However, the sensor is more resistant to sulfur at 1.6V than at 2.15V. These results indicate that poisoning is not a problem when the sensor is operated at V1=1.6 V.

TABLE 2

| Voltage (V) | 2.15 V | 1.60 V |
| --- | --- | --- |
| Signal fall after HMDS | −50 to −60% | −58% |
| Signal fall after H$_2$S | −50% | −17% |

The baseline drift was much slower at 1.6 V than at 2.15 V. In addition, the results showed that a catalytic bead sensor had much longer lifetime when it was operated at a voltage lower than the desired operating voltage.

The power at 1.6V is 146 mW, which is about 50% of the desired power at 2.15 V. The power will be further reduced if only the sensing bead is operated or pulsed power is applied.

The gas detector was calibrated with 2.5% methane/air (i.e. 50% LEL) at both 1.6 V and 2.15 V. The signal output was 50±1% LEL at 2.15 V and 50±5% LEL at 1.6 V, indicating that the signal accuracy at 2.15 V was much higher than that at 1.6 V.

What is claimed is:

1. A method for operating an instrument for detecting a combustible gas comprising a sensor including a heated surface on which the combustible gas reacts to cause a variation in an electrical parameter output, an electrical power supply for the instrument including a connection for heating the heated surface, a measuring unit for measuring gas concentration based on readings from the sensor and an output display for indicating the presence of a combustible gas, comprising the steps of:

providing means for actuating the power supply based on the electrical parameter measured by the measuring unit;

determining a first operating temperature T2 for the heated surface at which reaction of all types of combustible gas including methane takes place;

in the absence of a combustible gas, operating the instrument with the heated surface at a second operating temperature T1 at which combustible gas reacts on the heated surface and which is less than T2; and determining, with the measuring unit, changes in the electrical parameter output of the sensor, and further supplying power to the sensor such that:

when the sensor output is less than a predetermined threshold value, continuing to operate the sensor at temperature T1, and when the sensor output is at least equal to the threshold value indicating the presence of a combustible gas, increasing the temperature of the heated surface to T2, and operating at T2 during any time period when the electrical parameter is above the threshold value.

2. The method claim 1, wherein T2 is a desired operating temperature at which the sensor is operated under diffusion-limited conditions and has optimum stability and accuracy.

3. The method of claim 1, wherein T2 is about 500° C., and T1 is about 200–450° C.

4. The method of claim 3, wherein T1 is about 300–400° C.

5. The method of claim 1, wherein the sensor is a catalytic bead sensor.

6. The method of claim 5, wherein the sensor comprises a catalytic bead and a compensating bead.

7. The method of claim 5, wherein the sensor comprises a catalytic bead without a compensating bead.

8. The method of claim 1, wherein the sensor is a metal oxide semiconductor sensor.

9. The method of claim 1, wherein a change in at least one parameter selected from the group consisting of voltage, current and power is used to vary the temperature between T2 and T1.

10. The method of claim 1, wherein power from the power supply is provided in the form of pulses, with the duration of each of the pulses being sufficient either for the heated surface to reach at least temperature T1.

11. The method of claim 10, wherein the step of increasing the temperature of the heated surface to T2 comprises switching the power supply to a constant flow of electricity.

12. The method of claim 10, wherein the step of increasing the temperature of the heated surface to T2 comprises switching the power supply to pulses of a greater duration.

13. The method of claim 1, additionally comprising calibrating the instrument with a known concentration of a gas mixture at temperature T2.

14. The method of claim 13, wherein the instrument is additionally calibrated with a known concentration of a gas mixture at temperature T1.

15. The method of claim 1, additionally comprising periodically increasing the temperature from T1 to T2 to clean the heated surface.

16. The method of claim 1, wherein the temperature is changed between T1 and T2 by changing voltage supplied to the sensor.

17. The method of claim 6, wherein electricity is supplied to the compensating bead only when the heated surface of the catalytic bead is increased to temperature T2.

18. In an apparatus for detecting a combustible gas comprising a sensor including a surface heated to a predetermined temperature on which the combustible gas reacts to cause a variation in an electrical parameter output, an electrical power supply for the instrument including a connection for heating the heated surface, a measuring unit for measuring gas concentration based on readings from the sensor and an output display for indicating the presence of a combustible gas, the improvement comprising an actuating unit for controlling the power supply and a feedback link between the measuring unit and the actuating unit to provide gas concentration information to the actuating unit, wherein the actuating unit comprises means for heating the heated surface to a first temperature T1 at which combustible gas reacts on the heated surface, when combustible gas is detected at less than a predetermined concentration by the measuring unit, and heating the heated surface to a second temperature T2 which is greater than T1 when combustible gas is detected at or above the predetermined concentration.

19. The apparatus of claim 18, wherein the sensor is a catalytic bead sensor.

20. The apparatus of claim 18, wherein the catalytic bead sensor comprises a measuring bead and a reference bead.

21. The apparatus of claim 20, wherein the actuating means comprises means for operating the reference bead only when the combustible gas is detected at or above the predetermined concentration.

22. The apparatus of claim 18, wherein the sensor is a metal oxide semiconductor sensor.

23. The apparatus of claim 18, wherein the actuating means comprises means for adjusting voltage supplied for heating the heated surface between a lower voltage V1 corresponding to T1, and a higher voltage V2 corresponding to T2.

24. The apparatus of claim 18, wherein the actuating unit comprises means for supplying timed pulses of electricity for heating the heated surface, and for adjusting length of the pulses to change the temperature of the heated surface.

* * * * *